United States Patent [19]

Hausselt et al.

[11] Patent Number: 4,468,251
[45] Date of Patent: Aug. 28, 1984

[54] GOLD CONTAINING PREPARATION FOR COATING METALLIC PARTS (II)

[75] Inventors: Jürgen Hausselt, Langenselbold; Harry Schiwiora, Ispringen; Manfred Stumke, Pforzheim; Klaus Lutz, Rodenbach, all of Fed. Rep. of Germany

[73] Assignee: Degussa Aktiengesellschaft, Frankfurt, Fed. Rep. of Germany

[21] Appl. No.: 293,340

[22] Filed: Aug. 17, 1981

[30] Foreign Application Priority Data

Jul. 19, 1980 [DE] Fed. Rep. of Germany ....... 3027473

[51] Int. Cl.$^3$ .............................................. C09D 5/38
[52] U.S. Cl. .................... 106/1.18; 106/1.13; 106/1.14; 106/1.26; 106/35; 260/998.12; 524/430; 524/440; 524/439; 524/560; 524/574; 524/575; 433/218; 433/219; 433/220
[58] Field of Search ...................... 106/290, 1.05, 1.14, 106/1.13, 1.26, 1.18; 260/42.22, 998.12; 524/440, 430, 439, 560, 574, 575; 106/35; 433/220, 218, 219

[56] References Cited

U.S. PATENT DOCUMENTS

| | | | |
|---|---|---|---|
| 2,916,469 | 12/1959 | Lal | 260/998.11 |
| 2,980,998 | 4/1961 | Coleman et al. | 106/35 |
| 3,518,762 | 7/1970 | Takeuchi | 106/35 |
| 4,116,710 | 9/1978 | Heikel | 106/290 |
| 4,162,163 | 7/1979 | Subelka | 106/1.13 |
| 4,181,757 | 1/1980 | Youdelis | 106/1.18 |
| 4,230,493 | 10/1980 | Felter | 260/42.22 |
| 4,326,889 | 4/1982 | Sperner | 106/35 |
| 4,369,068 | 1/1983 | Hausselt et al. | 106/35 |

FOREIGN PATENT DOCUMENTS 0597662 3/1978 U.S.S.R. .......................... 106/1.05

*Primary Examiner*—Andrew Metz
*Assistant Examiner*—Margaret B. Medley
*Attorney, Agent, or Firm*—Cushman, Darby & Cushman

[57] ABSTRACT

There are applied gold containing preparations as intermediate layers for facing fired on alloys with ceramic compositions in the dental art. These gold preparations should improve the adhesiveness, form a structured surface and make possible a saving in the consumption of gold. This is accomplished with preparations that contain 60 to 95% gold powder, at least 50% of which are platelet shaped particles, 5-40% of a binder and in a given case up to 20 of a powder as an adhesive which is made of metals and/or non-metals.

13 Claims, No Drawings

GOLD CONTAINING PREPARATION FOR COATING METALLIC PARTS (II)

BACKGROUND OF THE INVENTION

The invention is directed to a gold containing preparation for coating metallic particles, particularly for coating fired on alloys in the dental art before the facing with ceramic compositions, consisting of gold powder, an adhesive and a binder of one or more organic solvents and one or more resin components, which binder is liquid at room temperature and volatilized or burned at firing temperature.

For many years in the dental art there has been known the facing of crowns and bridges made of fired on alloys with ceramic compositions. Thereby chiefly for aesthetic reasons the metallic crown or bridge framework is entirely or partially coated with one or more tooth colored ceramic layers. Likewise primarily for aesthetic reasons gold-rich intermediate layers are used which bestow a warmer colored background to the slightly transparent dental porcelain as is possible by the generally metallic white customary fired on alloys.

The previously known gold containing intermediate layer preparations lead to very smooth surfaces and cannot be effectively influenced by the dental technician.

The formation of the frequently desired grooves or relief type differences in height on the surfaces of the crowns and bridges thus is not possible. The previously known gold preparations were either melted or sintered and contain gold powder or ball-shaped gold particles (German AS 2851429) which leads to a uniform layer thickness and a very smooth surface.

On the other hand there has also long been known the significance of a sufficient dovetailing between the metallic fired on alloys and the dental ceramic for a good union. The preparation of the so-called physical union depends directly very strongly on the size, the shape and the roughness of the surface to be joined with the ceramic.

Besides all previously known preparations for intermediate layers have the disadvantage that they have a relatively high gold requirement of the great difficult in influencing the coating thickness.

Therefore it was the problem of the present invention to develop gold containing preparations for the coating of metallic portions, particularly for the coatings of fired on alloys in the dental art before the facing with ceramic compositions consisting of gold powder, an adhesive agent and a binder which is liquid at room temperature and is volatilized or burned at firing temperature, which after the firing guarantees the strongest possible dovetailing with the dental ceramic, has an aesthetic appearance and makes possible a saving in the use of gold.

SUMMARY OF THE INVENTION

This problem was solved according to the invention by a gold containing preparation made of 60 to 90 weight % gold powder which contains at least 50% of platelet shaped binder and 5 to 40 weight % of binder. Preferably the platelet shaped gold particles have a length and breadth dimension of less than 50μ and a thickness of less than 2μ, especially a length and breadth of less than 10μ and a thickness of less than 0.5μ.

It is advantageous if there is admixed with the gold preparation as an adhesive up to 20 weight % of a metal and/or inorganic non-metal powder whose particle size is between 10 and 100μ and whose melting point is above 1063° C., the melting point of gold.

Preferably the gold preparations contain 75 to 85 weight % gold powder, 15 to 25 weight % binder and 1 to 10% adhesive powder.

The binder generally consists of 60 to 90%, especially 65 to 80% of an organic solvent such as a glycol, glycol ether, glycol ester, terpene hydrocarbon, terpene alcohol or high boiling aliphatic hydrocarbon and 10 to 40%, especially 20 to 35% of a resin component such as acrylate resins, e.g. polymethylacrylate, polyethylacrylate or polybutylacrylate, methacrylate resins, e.g. polymethylmethacrylate or polybutylmethacrylate, nitrocellulose, ethylcellulose and natural or synthetic rubber, e.g. polyisobutylene, butadiene-styrene copolymer, polybutadiene or polyisoprene. As solvents there can be used for example glycols, e.g. ethylene glycol, propyleneglycol, diethyleneglycol or triethylene glycol, glycol ethers, e.g. the monomethyl ether of ethylene glycol, monomethyl ether of diethylene glycol, monoethyl ether of ethylene glycol, monoethyl ether of diethylene glycol or the monobutyl ether of diethylene glycol, glycol esters, e.g. ethylene glycol monoacetate or butyl diethylene glycol acetate, terpene hydrocarbons, e.g. limonene, camphane, pinene and terpinene, terpene alcohols, e.g. terpineol and high boiling aliphatic hydrocarbons, e.g. decane.

As adhesive powders above all there have proven good palladium, palladium alloys, gold alloys, cobalt, nickel and their alloys, aluminum oxide, silica, tin dioxide, indium oxide, cerium dioxide, yttrium oxide, titanium dioxide and titanium nitride. The alloy powder preferably contains the alloying elements which are also contained as alloying elements in the metallic parts to be coated, e.g. tin, indium, chromium, molybdenum, silicon, manganese, iron or mixtures thereof.

The preparations of the invention, which predominantly consist of platelet shaped gold can be applied in very thin layers to the parts to be coated, such as crowns and bridges, and consequently are extraordinarily saving. However, it has surprisingly been proven that these preparations with the help of customary application techniques with fine brushes permit attainment of an aimed for structurization of the surface which cannot be attained with previously known preparations. The control of the surface can be undertaken in practically any of the manners suitable to the dental technician for improvement of the anchoring and reinforcing the later ceramic layers, as e.g. in the form of grooves, reliefs or checkerboard pattern. These surface structures are maintained even after the firing of the preparation if the firing temperature is below the melting temperature of the gold. There have proven good firing on temperatures between 600° and 1040° C. and firing on times betweeen 1 and 10 minutes. The gold layers unite under these conditions with all current firing on alloys based on gold-platinum-palladium-silver, gold-palladium-silver, palladium-silver, gold-palladium, nickel-chromium, and cobalt-chromium to an indissoluble union. The gold containing preparations of the invention therewith are suited for all noble metal containing and noble metal free fired on alloys.

Furthermore it has turned out that the mentioned surface structure adjustable through the technique of application can be superimposed by an additional surface structure if the gold preparation are admixed with powdery additive made of metals and/or non-metals which are still present in the solid condition, i.e. not melted, at the firing temperature and which are coarser than the gold particles or platelets used. There have proven good ceramic additives of $Al_2O_3$, $SiO_2$, $SnO_2$, $In_2O_3$, $Y_2O_3$, $TiO_2$, TiN as well as metallic additives which have particle sizes above $10\mu$ but not greater than $100\mu$. Both the "coarse surface modulation" in the pure gold intermediate layers as well as the superimposing of the "coarse" and the "fine" surface structures in the preparations provided with additives effect an excellent anchoring of the ceramic layer with the metallic crown or bridge parts.

Thus investigations of ceramic faced alloy sheets which previously were coated with the preparations of the invention have shown that with forceful separation of the ceramic layer from the metal the break takes place in the ceramic itself. A separation of the intermediate layer from the fired on alloy or of the ceramic could not be observed in any case.

Unless otherwise indicated all parts and percentages are by weight.

The compositions can comprise, consist essentially of or consist of the stated materials.

Below there are set forth examples of several gold containing preparations according to the invention.

DETAILED DESCRIPTION

Example 1

80 weight % gold powder, platelet shaped $<10\mu$
16 weight % butyl diethylene glycol acetate
4 weight % nitrocellulose

Example 2

60 weight % gold powder, platelet shaped $<10\mu$
20 weight % gold powder, crystalline $<<10\mu$
16 weight % butyl diethylene glycol acetate
4 weight % polymethyl methacrylate

Example 3

75 weight % gold powder, plate shaped $<10\mu$
5 weight % $Al_2O_3$ powder, $<37\mu$
15 weight % terpineol
5 weight % ethycellulose

Example 4

75 weight % gold powder, platelet shaped $<5\mu$
5 weight % $AuPd_{10}Pt_5Sn_3In_2$ powder $<37\mu$
12 weight % high boiling aliphatic hydrocarbon
5 weight % polyisobutylene

Example 5

70 weight % gold powder, platelet shaped $<5\mu$
5 weight % powder made of $PdAu_2OSn_5$ $<20\mu$
18 weight % butyl diethylene acetate
7 weight % polymethylmethacrylate

Example 6

75 weight % Au powder, platelet shaped $<10\mu$
5 weight % Co powder $<20\mu$
16 weight % butyl diethylene acetate
4 weight % ethyl cellulose

What is claimed is:

1. A gold-containing preparation suitable for coating metallic parts especially for coating fired on alloys in the dental art before the facing with ceramic compositions, said preparation consisting essentially of (1) gold powder having length and breadth dimensions of less than $50\mu$ and a thickness of less than $2\mu$ and a binder of an organic solvent and a resin, said binder being liquid at room temperature and able to be volatilized or burned at the firing temperature, there being present 60 to 95 weight % gold powder of which at least 50% are platelet shaped particles and 5 to 40 weight % of the binder or (2) a preparation consisting eseentially of (1) and an adhesive.

2. A gold-containing preparation according to claim 1 wherein the gold platelets have length and breadth dimensions of less than $10\mu$ and a thickness of less than $0.5\mu$.

3. A gold-containing preparation according to claim 2 wherein there is present an adhesive, said adhesive being present in an amount of up to 20 weight % and consisting essentially of a metal powder, an inorganic non-metal powder or mixture of both a metal powder and an inorganic non-metal powder, said adhesive having a particle size between 10 and $100\mu$ and having a melting point above 1063° C.

4. A gold-containing preparation according to claim 1 wherein there is present an adhesive, said adhesive being present in an amount of up to 20 weight % and consisting essentially of a metal powder, an inorganic non-metal powder or mixture of both a metal powder and an inorganic non-metal powder, said adhesive having a particle size between 10 and $100\mu$ and having a melting point about 1063° C.

5. A gold-containing preparation according to claim 4 containing 75 to 85 weight % gold powder, 15 to 25 weight percent binder and 1-10 weight % adhesive powder.

6. A gold-containing preparation according to claim 3 containing 75 to 85 weight % gold powder, 15 to 25 weight percent binder and 1-10 weight % adhesive powder.

7. A gold-containing preparation according to claim 6 wherein there is used as the adhesive powder palladium, palladium alloy, gold alloy, cobalt, cobalt alloy, nickel, nickel alloy, aluminum oxide, silica, tin dioxide, indium oxide, cerium dioxide, yttrium oxide, titanium dioxide or titanium nitride.

8. A gold-containing preparation according to claim 5 wherein there is used as the adhesive powder palladium, palladium alloy, gold alloy, cobalt, cobalt alloy, nickel, nickel alloy, aluminum oxide, silica, tin dioxide, indium oxide, cerium dioxide, yttrium oxide, titanium dioxide or titanium nitride.

9. A gold-containing preparation according to claim 2 containing 1 to 20% of an adhesive powder and wherein there is used as the adhesive powder palladium, palladium alloy, gold alloy, cobalt, cobalt alloy, nickel, nickel alloy, aluminum oxide, silica, tin dioxide, indium oxide, cerium dioxide, yttrium oxide, titanium dioxide or titanium nitride.

10. A gold-containing preparation according to claim 1 containing 1 to 20% of an adhesive powder and wherein there is used as the adhesive powder palladium, palladium alloy, gold alloy, cobalt, cobalt alloy, nickel, nickel alloy, aluminum oxide, silica, tin dioxide, indium oxide, cerium dioxide, yttrium oxide, titanium dioxide, or titanium nitride.

11. A gold-containing preparation according to claim 7 wherein the binder contains 10 to 40 weight % resin and 60 to 90 weight % solvent.

12. A gold-containing preparation according to claim 6 wherein the binder contains 10 to 40 weight % resin and 60 to 90 weight % solvent.

13. A gold-containing preparation according to claim 3 wherein the binder is made up of 20 to 35% resin and 80 to 65% of solvent.

* * * * *